United States Patent [19]

Horan

[11] Patent Number: 5,415,180

[45] Date of Patent: May 16, 1995

[54] SYSTEM AND KIT FOR MEDICAL PROCEDURES

[75] Inventor: Robert T. Horan, Northridge, Calif.

[73] Assignee: Devon Industries, Inc., Chatsworth, Calif.

[21] Appl. No.: 147,337

[22] Filed: Nov. 3, 1993

[51] Int. Cl.⁶ .................. A61F 5/37; A61B 19/00; A47G 19/00

[52] U.S. Cl. .................. 128/846; 128/849; 220/23.4

[58] Field of Search ............. 128/845, 846, 849–856; 220/23.83, 83, 23.3, 23.4; 206/570; 4/550, 655, DIG. 13; 493/916; 224/4; 338/118

[56] References Cited

U.S. PATENT DOCUMENTS

| Re. 4,865 | 4/1872 | Stuart. | |
|---|---|---|---|
| 1,490,353 | 4/1924 | Wagemaker. | |
| 3,697,223 | 10/1972 | Kovalick et al. | |
| 4,221,295 | 9/1980 | Tuchband | 206/569 |
| 4,241,833 | 12/1980 | Luebcke | 206/570 |
| 4,395,454 | 7/1983 | Baldwin | 128/849 |
| 4,925,047 | 5/1990 | Valentine | 220/23.83 |
| 4,934,152 | 6/1990 | Templeton | 128/846 |
| 5,072,832 | 12/1991 | Valentine et al. | |

Primary Examiner—Michael A. Brown
Attorney, Agent, or Firm—Poms, Smith, Lande & Rose

[57] ABSTRACT

An easily assembled system for handling surgical instruments includes as components (a) a waterproof container sized to fit into a ring of a conventional surgical ring-stand; (b) a waterproof expandable wrap sized to fit over such a ring prior to insertion of the container; and (c) a flexible, pliant, porous cradle, with handles, sized to fit into the container. The floor of the cradle is porous with respect to the sterile solution used to fill the container-cradle combination and into which bloodied surgical instruments are deposited. The cradle facilitates removal of the instruments by containing them when it is lifted out of the container, during which the now murky solution drains completely out of the cradle and into the container. The handles may be strengthened against tearing by three-dimensional curvilinear molding which pre-biases the handles and adjacent portions of the rim against the stress-pattern engendered by lifting significant masses of solids and undrained liquids. The cradle, wrap, and container may be fabricated of sterilization-tolerant material and sterilized in situ after being sealed inside a delivery package, as part of a pre-packaged kit, which provides convenient storability to the system prior to its assembly and deployment.

10 Claims, 3 Drawing Sheets

SYSTEM AND KIT FOR MEDICAL PROCEDURES

FIELD OF THE INVENTION

This invention relates to the field of operating room surgical instruments and devices for handling such instruments before, during and after a medical procedure, and, more particularly, as regards handling before a procedure, to the sub-field of compactly storable and disposable instrument-handling systems and prepackaged kits thereof.

BACKGROUND OF THE INVENTION

Traditionally nurses deposit bloodied surgical instruments into a container of sterile solution immediately after use, for later retrieval and sterilization (regarding which numerous options are available). The intention of this post-use procedure is to keep the blood from drying on the instruments, which is undesirable for several reasons (including the fact that the proteins in the blood attack stainless steel).

However, the blood has a tendency to render the originally sterile solution cloudy or murky, and to render it difficult or impossible to see the instrument or instruments which have been deposited into the container. Moreover many such instruments are extraordinarily sharp and if a person reaches for an instrument which cannot be seen clearly, there is grave danger of an accidental occupational exposure, such as a cut or puncture, to health-care personnel.

Moreover, the recent increase in accidents in which health-care personnel have been accidentally infected with hepatitis or HIV virus has caused the federal government to generate new OSHA-mandated safety requirements directed at eliminating the possibility of such life-threatening accidents.

Accordingly there exists an urgent need for modification of the traditional handling techniques in order to maximally reduce the possibility of handling accidents.

Also there exists a concomitant need to introduce modified handling techniques compatible with maximal flexibility as regards the choice of subsequent sterilization techniques (four different methods of which now have widespread adoption, with no one method being universally preferred).

Finally, in case a convenient solution to the preceding problem and other closely-related operating room problems can be provided by the organized and systematic use of an easily-assembled combination of devices comprising altogether a new system for medical procedures, there exists an obvious need for a complete, unified set of the component devices of such a system to be available as an integrated combination in a sterilized, storable, prepackaged kit which can be maintained as a compact and sterile unit until actual opening of the package and assembly is required.

SUMMARY OF THE INVENTION

In accordance with the principles of the present invention, there is provided a system comprising the coordinated use of the following four components:

(1) at least one waterproof, expandable, plastic wrap, sized to fit across a conventional one-ring or two-ring surgical stand;

(2) at least one waterproof rigid basin sized to fit inside of a ring of a conventional ring-stand;

(3) at least one waterproof liner made of flexible, pliant, high-temperature tolerant material, which fits into such a basin after the wrap has been spread across the basin and pushed into it, thereby providing a barrier between the (optionally sterile) liner and the possibly non-sterile basin and the non-sterile ring-stand;

(4) a cradle made of flexible, pliant, high-temperature tolerant material which fits into either the liner or the basin (hereinafter referred to as a "container", meaning either), and is sufficiently porous that the bloodied water will drain rapidly into the container when the cradle is lifted, by means of integral handles, from the container while retaining any deposited instrument within itself.

In practice, if the preceding components are provided as a kit, then there will be two classes of kits, one containing a basin but no liner and the other containing a liner but no basin. In other words, in the presently preferred embodiments of this invention, the providing of a basin and the providing of a liner are normally taken to be mutually exclusive options.

In accordance with a further aspect of the invention, the cradle and liner and wrap may each (optionally) be sufficiently pliant that it could be folded and stored compactly prior to use, if desired.

In accordance with a still further aspect of the invention, keeping in mind that usually the liner and basin are mutually exclusive, the cradle and the liner and the wrap and the basin may each (optionally) be made of sufficiently inexpensive material that it is disposable after use; also the choice of material for each (as, if possible, biodegradable [e.g. cellulosic], or at least of small volume) is made in the light of environmental protection concerns.

In accordance with a still further aspect of the invention, the cradle and liner and wrap and [optionally, the] basin is each made of a sterilization-tolerant material, so that it can be sterilized (e.g. by gamma-ray irradiation, or steam heating, or antiseptic gas) and sealed inside of a sterilized pliable bag or package prior to delivery and storage near the operating room. This can also be done with a kit containing the cradle plus at least any two of the following three components of the system, (all three of which are adapted to fit a conventional ring-stand), namely: (1) the watertight expandable plastic wrap; (2) the rigid watertight basin into which the cradle fits; and (3) the watertight pliable liner into which the cradle also fits. Similarly this can be done with a kit containing the cradle and a wrap plus either a liner or a basin. Finally, this can be done with a kit containing the cradle and wrap and both a liner and a basin, although there is expected to be much less demand for this quadruple combination than for the preceding triple combinations.

Other objects, features, and advantages will become apparent from a consideration of the following detailed description and from the accompanying drawings.

DETAILED DESCRIPTION OF PRESENTLY PREFERRED EMBODIMENTS

Figure 1:
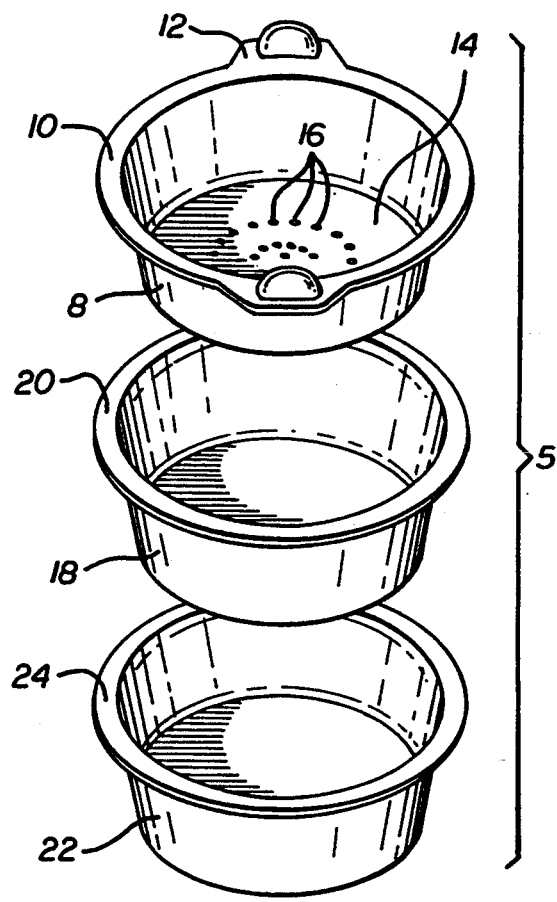
FIG. 1 is an exploded perspective view of the pliable porous cradle in one possible relationship to a rigid wash basin and to a possibly present disposable, pliable watertight liner which is sometimes placed between the cradle and the basin (but only if a sterile barrier such as a waterproof expandable wrap is first placed between the basin and the line)
Figure 2:
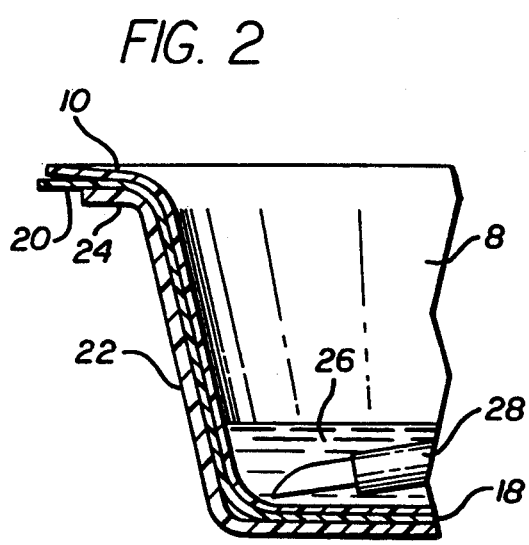
FIG. 2 is a cutaway side-view drawing, showing the option of placement of the cradle within a liner which in turn is within the basin, as well as initially sterile solution containing a bloodied surgical instrument; however, it should be noted that in the present invention there would always be a wrap or barrier between the basin and the liner which is not shown in this FIG. 2, which is meant only to illustrate the operation of the cradle and not the aspect of the present invention involving the wrap.
Figure 3:
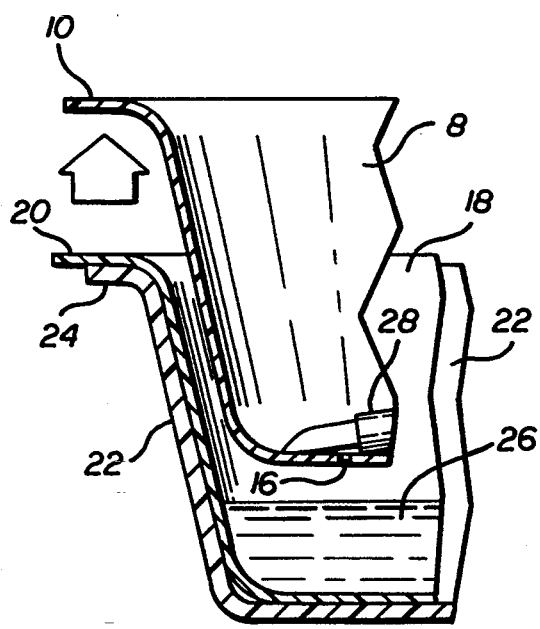
FIG. 3 shows the cradle partially lifted out of a liner (if present), into whose basin the water flows, while leaving the surgical instrument contained in the cradle (and, as mentioned in connection with the preceding two Figures, this drawing is meant to illustrate only the operation of the cradle, and therefore neglects to depict the wrap which in accordance with the principles of the present invention, should form a barrier between the basin and the liner, if a liner is used, or, at least, form a barrier between the ring-stand and the basin in case the liner is not used)

Referring more particularly to the drawings, FIG. 1 shows one possible configuration 5 of a subsystem of the system 6 of the present invention (shown in FIG. 4); the subsystem 5 is the system of the cradle 8 in relationship to a rigid container 22 and a possibly present liner 18. In the sequel the words "basin" and "liner" shall both refer only to some form of a container which is water-tight; the word "basin" shall imply that the container is rigid (such as when formed of metal or rigid plastic), whereas the word "liner" shall be used interchangeably with "container made of flexible, pliant material". Furthermore, under ordinary conditions the basin and the liner will not be provided simultaneously, except under relatively rare circumstances which will be explicitly mentioned; absent explicit exception, it will be assumed that the liner and the basin are mutually exclusive.

It should be noted that the principal requirements pertaining to the cradle 8 (which is, alone, the subject of a separate copending patent application assigned to the assignee of this invention) are that it must be flexible, pliant, and porous; it may or may not include handles 12 and a possible but not required rim 10. (Certain improvements in the method of manufacturing the handles 12, pertaining to strengthening them against tearing, are the subject of a separate copending patent application assigned to the assignee of this invention.) The cradle 8 can function in the absence of the optional liner 18, which may not be present, in which case the cradle 8 is used with a basin 22 alone and the subsystem 5 is composed of two rather than three components. Alternatively, in the subsystem 5 the basin 22 may not be present, and a more-or-less flexible containment system (composed of one or a plurality of nested liners 18) may provide the same function as a single primary container 22 or 18. (In this case it would be usual for a basin to have been present and available as part of the ring-stand, not as part of the present invention.) Furthermore, even if all three elements (8, 18, and 22) of the subsystem 5 depicted in FIG. 1 are present, they can be stored prior to use in any order whatsoever. Also the depiction of the subsystem 5 in conjunction with possibly present and possibly functionally related but not separately herein claimed accessories (as in FIGS. 1-9) is not meant to imply that any such accessory, present or absent, [such as a liner, a basin, a wrap, or a ring-stand] is part of the present subsystem 5; rather, the use of the cradle 8 in conjunction with at least two of the first three listed such possible accessories is a presently preferred embodiment of the complete and herein disclosed system 6; the cradle 8 is also one of the components of a kit providing the system 6 in a self-contained, storable, sterile, prepackaged, readily-assembled form.

Accordingly, in one presently preferred embodiment of the present invention 6, the size and shape of the cradle 8 is selected (as a conical frustum) such that it can be nested within a standard basin 22 and/or a standard liner 18 (and/or a flexible basin system, such as described above, but not shown). Generally such basins and/or liners have the shape of a conical frustum (or, more colloquially, a "truncated tapered cylinder"), which means for practical purposes that any one of the three elements of the particular depicted exemplary subsystem 5 can be nested either within or without any of the other three elements. Accordingly there are 3!=6 ["three factorial"=3.2.1=6], or six different orders in which the three elements of subsystem 5 could have been arranged in a vertical array, and the exploded drawing of the three elements in the vertical order depicted is not meant to imply that the present subsystem 5 could not be used in conjunction with any of the remaining five orders not depicted. The same point should be taken into account in viewing FIG. 2 and FIG. 3 (namely that the orders of the liner 18 and the basin 22 could be interchanged, or either 18 or 22 could be omitted and reliance placed solely upon use of the cradle 8 in conjunction with the remaining alternative container [either 22 or 18], without departing from the scope of the present invention 6 of the system including the subsystem 5, and therefore the cradle 8; likewise, mutatis mutandis, the same point about immateriality of any rearrangement of the depicted order of the cradle and a basin [if any] and a liner [if any] and a wrap [if any] applies to FIGS. 4-7, as will become apparent below. The reason that the basin 22 may or may not be part of the claimed system 6 and prepackaged kit 34 thereof is that the basin 22 may already be present in connection with the externally provided single-ring stand 32 (or two-ring stand 42), in which case its inclusion in the kit 34 as optional basin 37 would become superfluous.

Despite the preceding restrictions on the shape of the components 8, 18 and 22 in a presently preferred embodiment, the presently disclosed subsystem 5 could be adapted readily to any chosen form of liner 18 or basin 22, whether either of the latter containers has substantially the shape of a conical frustum or not. For example, the cradle 8 can be made sufficiently pliant that, by accepting overlapping folds of its walls and/or floor 14 and rim 10, it can be used in conjunction with a liner 18 or basin 22 whose size and shape is radically different from the standard "rounded conical frustum" depicted in FIGS. 1–9.

That having been said, the following discussion will relate to a very few particular examples of presently preferred embodiments in order to achieve clarity for the reader's convenience.

Thus, consider a cradle 8 made of a flexible and pliant material which can be arranged or configured as shown in FIG. 1 with a rim 10 which overlaps either the rim 20 of the liner 18 or the rim 24 of the basin 22 (or both, if both are present). The subsystem 5 of the invention 6 will work whether or not the liner 18 or the basin 22 has a rim, but a presently preferred embodiment of the subsystem 5 itself does include a rim 10 on the cradle 8, in order that handles 12 may be incorporated in it. (However, in an alternative embodiment, the cradle 8 could be configured to have no rim, but to have apertures functionally equivalent to handles provided in portions of its upper periphery which remain above the waterline of any fluid which may be contained in the liner 18 or basin 22.) See also the planform view of the cradle 8 shown in FIG. 8, and its cutaway vertical cross-section shown in FIG. 9. Further details of the handles 12 will be discussed below.

Figure 8:
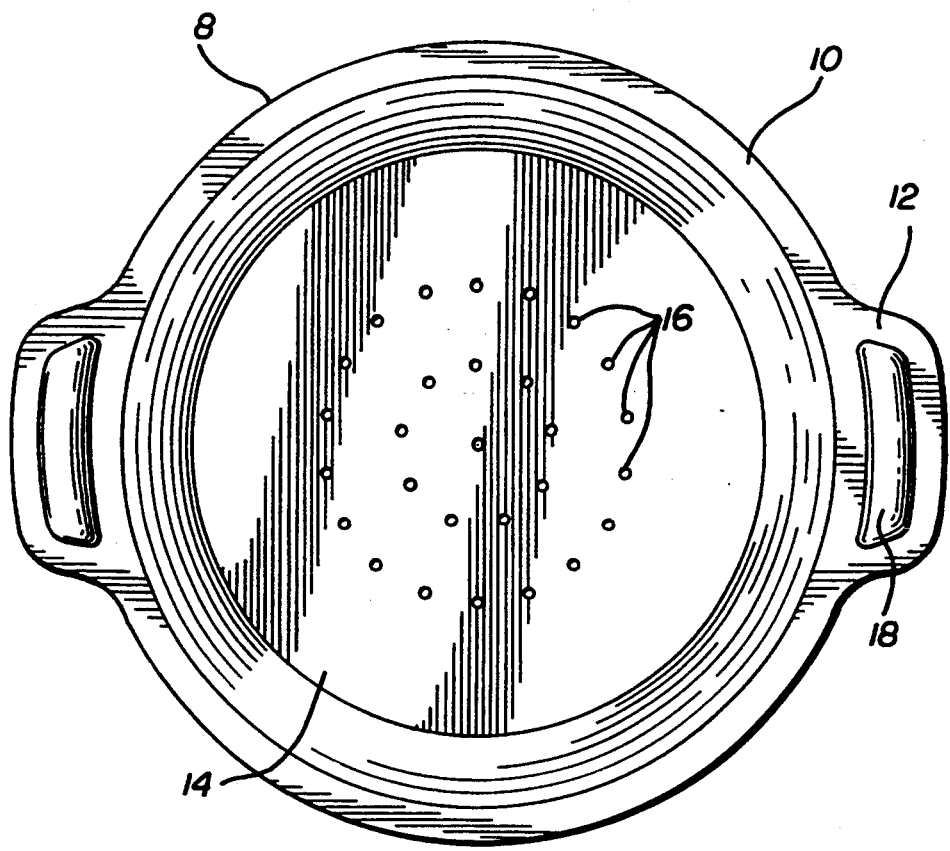
FIG. 8 is a horizontal planform view of the cradle in an embodiment including a rim and handles as well as porosity elements.

As shown in FIG. 8, the most important feature of the cradle 8 shall be called its "porosity elements" 16. Although these elements are depicted as macroscopically visible holes in FIGS. 1 and 8, which in a presently preferred embodiment permit the aqueous solution of blood and water to drain from the cradle 8 in about seven seconds, the subsystem 5 of the system 6 can be implemented successfully with pliable materials whose porosity elements are too small to be visible with the unaided eye as identifiable apertures or openings into the surface of the material; likewise the porosity elements need not comprise holes which penetrate straight through from the upper surface to an entrance at the lower surface, but rather can be formed of linked channels through which water entering apertures on the upper surface will eventually drain (by gravity) through apertures on the bottom surface. In the case of small porosity elements, however, they must be sufficiently numerous that the collective effect is to allow rapid drainage through the cradle 8. Consequently it is the criterion of enabling relatively rapid drainage through the cradle 8 rather than any other geometrical or physical property which is the basic defining characteristic of "porosity elements". A secondary consideration in addition to rapid drainage is the allowance of selected categories of particulate wastes to be drained along with the fluid solution; for this reason, one preferred embodiment incorporates porosity elements comprised of substantially circular holes of about ⅛ of an inch in diameter.

As shown in FIG. 8, the porosity elements 16 may cover the entire floor 14 of the cradle 8, or they may be restricted to a central portion of the floor 14, leaving a solid annular margin of the floor surrounding the porosity elements 16. The hydrodynamic flow configuration generated by this restriction keeps the liquid solution centralized and prevents accidental occupational exposure of health-care personnel by splashing or spraying (which otherwise can be engendered accidentally by distortion of the pliant rim 10 during manual lifting of the flexible, pliant cradle 8).

The cradle 8 is chosen to enable at least four separate post-drainage approaches to sterilization of the instruments which it contains:

(1) the cradle 8 may be placed directly into an autoclave or washer-sterilizer or the like, because the material of which it is fabricated can withstand temperatures of the order of 275 degrees Fahrenheit without weakening significantly;

(2) the cradle 8 may be placed directly into an ultrasonic cleaner which removes particles from the metal surgical instruments by acoustic shock waves;

(3) the bilateral symmetry created by placement of handles 12 in extensions of the rim 10 on diametrically opposite sides of the periphery of the rim 10 enables the instruments to be slid or "poured" out upon a flat work-surface or floor of a sink by an operator who need never touch the instruments but merely grasps the opposing handles 12 in order to lift, carry, and deposit the instruments contained in the cradle 8, thus conveniently enabling the instruments to be rinsed under a faucet in a sink, prior to autoclave sterilization;

(4) after the exit of the murky water, the instruments contained on the floor 14 of the cradle become sufficiently perfectly visible that it is possible, with care, for a human to pick up each instrument for hand-washing over a sink, prior to autoclave sterilization.

Figure 4:
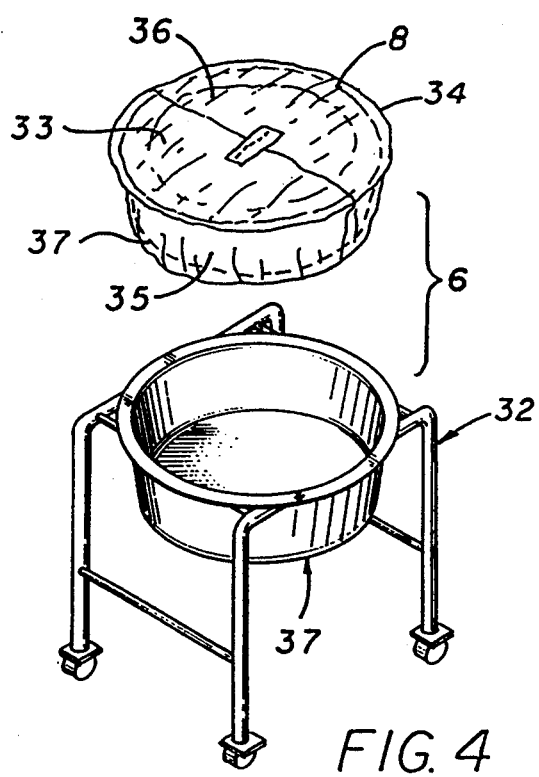
FIG. 4 depicts another configuration into which the cradle may be incorporated, as an element of the system of the present invention, and as a component of a sterilized kit adapted to be applicable to conventional ring-stands, which contains a wrap, a cradle, and either a liner or a basin.
Figure 5:
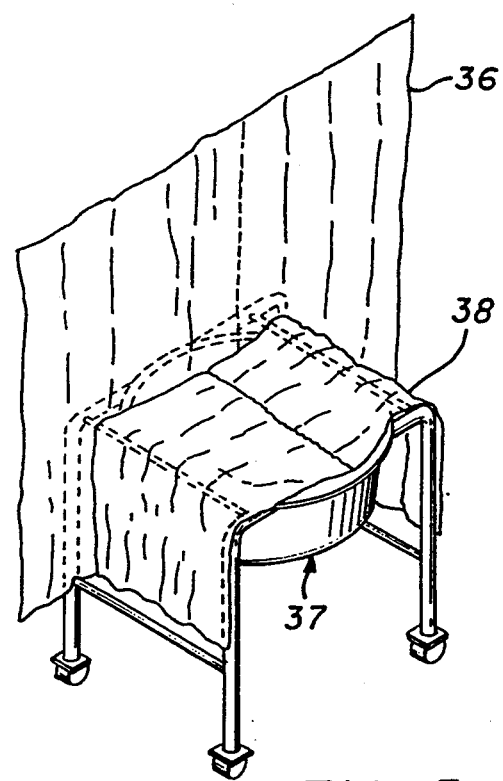
FIG. 5 shows one of the components of the kit of FIG. 4, namely the expandable, waterproof, sterile plastic wrap, both displayed as to expanded, unwrapped size, and as draped over a conventional ring-stand after insertion of the basin of FIG. 4 but prior to insertion of the liner of FIG. 6.
Figure 6:
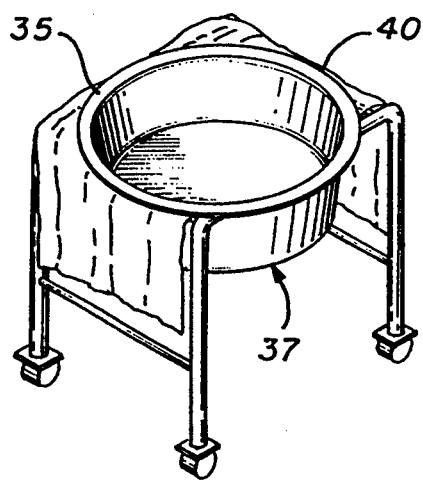
FIG. 6 shows still another component of the kit of FIG. 4, namely the flexible, pliant waterproof container, or liner, adapted to fit into the ring-stand after the basin of FIG. 4 has been inserted into the ring and after the ring has been covered with the wrap of FIG. 5, and before the cradle of FIGS. 1-3 has been fitted into the liner (as in FIGS. 1-3)
Figure 7:
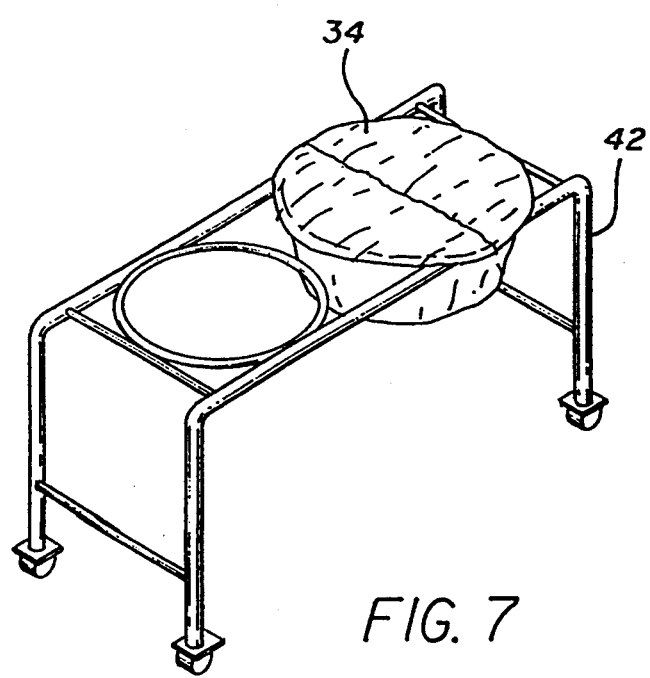
FIG. 7 shows the kit of FIG. 4 in conjunction with a conventional two-ring stand, to which it is also applicable.

In one presently preferred embodiment of the present invention as a prepackaged kit 34, sealed in a plastic bag or package 33, the cradle 8 is a component of a subsystem 5 of kit 34 which is to be used as part of a configuration including a conventional ring-stand 32, as shown in FIG. 4. The kit 34 includes not only the cradle 8 (depicted as a phantom structure) but also, optionally, a liner 35 of the type previously discussed as liner 18 (also shown as a phantom structure, into which the cradle 8 has been fitted), and, again optionally, an expandable, waterproof plastic wrap 36, and, possibly and again optionally, a rigid basin 37, such as is shown fitted into a ring of an externally-provided single-ring ringstand 32. All three primary optional components (8, 35, 36) of the kit 34 may be fitted together or enfolded compactly and, possibly with or without an optional basin 37, which may or may not be externally provided, sealed inside of an airtight plastic bag or other sealable package 33, the interior of which may be sterilized (e.g. by gamma-ray irradiation, or steam heat, or antiseptic gas) prior to delivery and use in conjunction with a single-ring ringstand 32 as depicted in FIGS. 4, 5 and 6, or with a multiple-ring ringstand 42 as depicted in FIG. 7. Whether or not the basin 37 is provided as part of the kit 34, it is assumed available for use in connection with a ringstand in FIGS. 4–7, because the liner is insufficiently rigid to function as a basin alone.

The wrap 36 may be unfolded and expanded to the size shown in FIG. 5, and then draped over the ring, after the basin 37 has been fitted into it, as draped-wrap 38 of FIG. 5. Then the liner 35 may be inserted into the ring, pushing the wrap 36 below it, and into the basin 37, as shown in FIG. 6. To be explicit: in this presently preferred alternative embodiment, the basin 37 is assumed to be part of the externally-provided ring-stand 32 or 42, and the system of the invention comprises the insertion into such a basin of the wrap 36, followed by insertion into the basin and over the wrap of the liner 35, followed by insertion into the liner of cradle 8. Subsequently the cradle 8 may be used in conjunction with the liner 35 as already explained in connection with the liner 18 of FIGS. 1-3.

In an alternative presently preferred embodiment, depicted in FIG. 7, the kit 34 may consist of a package 33 containing only a sterile cradle 8, a sterile wrap 36, and a sterile basin 37. In this embodiment, the wrap 36 is first placed over the non-sterile ring-stand, to form a sterile barrier between the ring-stand and the sterile components, after which the sterile basin 36 is inserted into the ring-stand through the loosely-draped wrap 36, and then the sterile cradle 8 is inserted into the basin 37. Subsequently the cradle 8 may be used in conjunction with the basin 37 as already explained, analogously, in connection with the liner 18 of FIGS. 1-3.

In either of the presently preferred alternative kit embodiments 34 just mentioned, the cradle and liner or cradle and basin may be enfolded within the expandable wrap; however, in the presently preferred embodiments of the kit 34, neither the liner itself nor the cradle itself will be folded.

Figure 9:
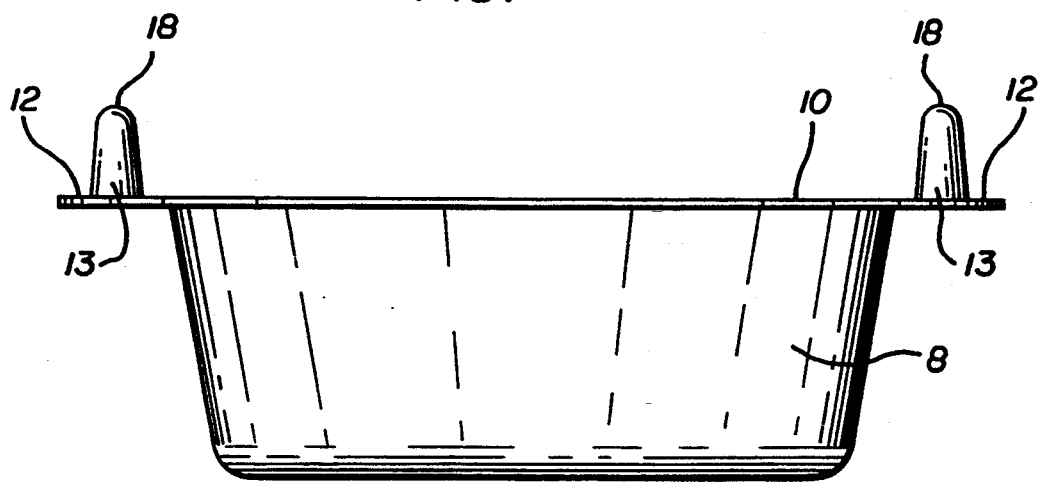
FIG. 9 is a cutaway vertical cross-section of the cradle of FIG. 8 depicting certain details of the manufacture of the handles in one presently preferred embodiment.

An important feature of a presently preferred embodiment of the cradle 8 is the tear-resistant handles 12, depicted schematically in greater detail in FIGS. 8 and 9. If the handles are made flat as shown in FIG. 1, they will often lack sufficient strength not to tear when a full load of solution and instruments is lifted out of the liner 18 or basin 22. This problem can be eliminated by providing a three-dimensional curvilinear bias in the material adjacent to and within the handle, as depicted in FIG. 9, wherein the empty gap or hollow 13 is created in the handles 12 by means of appropriate three-dimensional molding procedures. This pre-biased nature of the pliant material of which the cradle 8 is molded is selected to reduce any additional tendency to stretch the material during the stress pattern engendered by the lifting of significant masses of solids and undrained liquids when the cradle is used. (An engineering stress analysis technique for optimizing the design of the "prebias" geometry, which typically requires the periphery of the handles 12 to have non-vanishing Gaussian curvature—even though the remainder of the tapered-cylindrical surface of the sides of cradle 8 is "flattenable" and so has vanishing Gaussian curvature—will be found in the cited copending application pertaining to strengthening of the handles 12.)

RAMIFICATIONS, SCOPE AND CONCLUSION

In conclusion, it is to be understood that the foregoing detailed description, and the accompanying drawings relate to the presently preferred illustrative embodiments of the invention. However, various changes may be made without departing from the spirit and the scope of the invention. Thus, by way of example and not of limitation, the porosity elements 16 may cover not only the central disk of the floor 14 of the cradle 8, but may cover the entire floor 14, and may even extend up the sides of the cradle 8 as well; in fact, the entirety of the cradle can be covered with porosity elements without departure from the scope of the invention disclosed herein.

Furthermore, it is possible to use different and even composite materials to fabricate each of the cradle 8, liner 35, wrap 36, optional basin 37 and (in the case of a kit 34 rather than the system 6), sealable bag or package 33, instead of integral molding of each in synthetic polymers such as the presently preferred thermoplastic polyolofin resin materials. In addition, the parts (i.e. rim 10 [if any], handles 12, floor 14, and porosity elements 16) need not have the precise configuration described hereinabove, but may have alternative arrangements which accomplish substantially the same functions in substantially the same way.

Also it is possible to choose all of the materials of which each of the cradle 8, liner 35, wrap 36, optional basin 37 and (in the case of a kit 34 rather than the system 6), sealable bag or package 33, is separately fabricated to be sufficiently sterilization-tolerant that each can be sterilized in situ (as by steam heat, or by antiseptic gas, or by gamma-ray irradiation after being sealed inside of a plastic bag or other airtight package 33). Furthermore the cradle 8 may be enfolded together with an expandable, waterproof plastic wrap 36 (of a known type) and with a pliant, flexible liner 35 (of the known type 18 explained above) and all three components may be sealed inside of a subsequently sterilized bag or package 33 as part of a kit 34 adapted for use in connection with a conventional one-ring ringstand 32 or a multiple-ring ringstand 42. Alternatively a rigid basin 37 may be included in such a kit 34 instead of (or even in addition to) a liner 35, but in one presently preferred embodiment the basin is assumed to be externally available and not included in the kit 34.

Accordingly, it is to be understood that the detailed description and the accompanying drawings as set forth hereinabove are not intended to limit the breadth of the present invention, which should be inferred only from the following claims and their appropriately construed legal equivalents, rather than from the examples given.

I claim:

1. An easily-assembled system for enhancement of safety and convenience in the handling of operating room surgical instruments, in conjunction with a surgical ring-stand containing at least one ring, said system comprising:

(a) a flexible, pliant, porous cradle including externally accessible handles thereto;

(b) a waterproof, expandable, plastic wrap sized to fit over said surgical ring-stand;

(c) a waterproof container sized to fit into said surgical ring-stand after said wrap has been placed over a ring of said ring-stand, and sized to contain the porous portion of said cradle;

the combination of said components, when assembled, providing a containment system for a sterile solution into which bloodied instruments may be deposited, and by means of which said deposited instruments may be retrieved from said solution by use of said handles to remove said cradle after the deposition of said instruments therein, while allowing said solution to drain from said cradle into said container by means of said porosity of said cradle.

2. The system of claim 1 wherein said components (a), (b), (c) are made of sterilization-tolerant materials.

3. A kit comprising the unassembled components (a), (b), (c) of the system of claim 2, sterilized and contained within a sealed, storable, sterilized package as a pre-packaged kit enabling rapid and convenient assembly and deployment of the system of claim 2 when needed, and convenient storage of said components prior to said deployment.

4. The system of claim 1 wherein said cradle is made of high-temperature tolerant material.

5. The system of claim 1 wherein said cradle is made of a synthetic polymer.

6. The system of claim 5 wherein said synthetic polymer is selected from the class of thermoplastic polyolofin resin materials.

7. The system of claim 1 wherein said component (c) comprises a waterproof liner made of flexible, pliant material and sized to fit into a rigid basin, assumed available, which fits into a ring of said ring-stand and is separated from said liner by a barrier comprised of said wrap (b) which is draped loosely over said basin prior to insertion of said liner into said basin through said wrap.

8. The system of claim 7 wherein said liner is made of high-temperature tolerant material.

9. The system of claim 7 wherein said liner is made of a synthetic polymer.

10. The system of claim 9 wherein said synthetic polymer is selected from the class of thermoplastic polyolofin resin materials.

* * * * *